United States Patent
Sarhan et al.

(10) Patent No.: US 12,210,015 B2
(45) Date of Patent: Jan. 28, 2025

(54) METHODS TO REGISTER AND INTERPRET LATERAL FLOW TEST STRIP ASSAY MEASUREMENTS BY TRANSMISSION OF MULTI-WAVELENGTH VISIBLE AND NEAR-VISIBLE LIGHT

(71) Applicants: Sameh Sarhan, Santa Clara, CA (US); Lawrence Herbert Zuckerman, Livermore, CA (US)

(72) Inventors: Sameh Sarhan, Santa Clara, CA (US); Lawrence Herbert Zuckerman, Livermore, CA (US)

(73) Assignee: Xtrava Inc., Santa Clara, CA (US)

( * ) Notice: Subject to any disclaimer, the term of this patent is extended or adjusted under 35 U.S.C. 154(b) by 97 days.

(21) Appl. No.: 17/107,903

(22) Filed: Nov. 30, 2020

(65) Prior Publication Data
US 2021/0164975 A1 Jun. 3, 2021

Related U.S. Application Data

(60) Provisional application No. 62/942,694, filed on Dec. 2, 2019.

(51) Int. Cl.
*G01N 33/543* (2006.01)
*G01N 21/27* (2006.01)
*G01N 21/64* (2006.01)
*G01N 21/84* (2006.01)

(52) U.S. Cl.
CPC ..... *G01N 33/54388* (2021.08); *G01N 21/274* (2013.01); *G01N 21/6428* (2013.01); *G01N 21/8483* (2013.01); *G01N 2021/6439* (2013.01)

(58) Field of Classification Search
CPC ......... G01N 21/8483; G01N 33/54388; G01N 21/274; G01N 21/6428; G01N 2021/6439
See application file for complete search history.

(56) References Cited

U.S. PATENT DOCUMENTS

2006/0098203 A1* 5/2006 Kalveram .......... G01N 21/8483
356/446
2018/0306709 A1* 10/2018 Zaccari .............. G01N 21/6456

* cited by examiner

*Primary Examiner* — Brian J. Sines
(74) *Attorney, Agent, or Firm* — AVEK IP, LLC

(57) ABSTRACT

A method, apparatus and system that illuminates one face of a lateral flow assay test strip or test strip assembly with light of selected wavelengths and intensities and measures the resulting light intensities at the opposite face at the test stain line region and adjacent regions, in order to determine the value of analyte concentration over an extremely wide range, including values too small to produce a visible test stain line.

4 Claims, 10 Drawing Sheets

Illumination Source not shown but is in the extreme background projecting light toward the opposite face of the test strip, in the direction of the person viewing the instant figure.

FIG 10 ial Application 62/942,694, filed 2 Dec. 2019, which is incorporated by reference.
METHODS TO REGISTER AND INTERPRET LATERAL FLOW TEST STRIP ASSAY MEASUREMENTS BY TRANSMISSION OF MULTI-WAVELENGTH VISIBLE AND NEAR-VISIBLE LIGHT

CROSS-REFERENCE TO RELATED APPLICATION

Priority is claimed under 37 CFR 1.78 and 35 USC 119(e) to U.S. Provisional Application 62/942,694, filed 2 Dec. 2019, which is incorporated by reference.

TECHNICAL FIELD

This disclosure relates generally to instruments that determine the presence and/or quantity of chemical compounds. More specifically, this disclosure relates to automated assay instruments that use the lateral flow technique.

BACKGROUND

For at least 50 years, the lateral flow assay method has been known for its ability to provide handy determination of the presence and concentration of various substances. Before 1960, in a somewhat related method called electrophoresis, samples containing a mixture of proteins were deposited on absorbent paper strips and later, on gel media. An electric field or potential was applied to the medium, causing proteins of various charge values to migrate at different speeds, thus separating them as a fractionation procedure. Although the most familiar applications for the lateral flow assay method are pregnancy tests, the method is used for a significant variety of additional tests and in many industries.

The principal values of the lateral flow assay method are low cost, portability, and ease of use, including by those who are unskilled in the practice analytical chemistry. A liquid sample, that may or may not contain a target chemical compound, "analyte" is applied close to one end of a test strip consisting of absorbent material that draws the sample by capillary action through the entire length thereof, wetting the strip as it proceeds.

If and only if the sample contains the target analyte compound, chemical means keyed to it at a fixed "test line" position along the strip causes a visible "stain" line to be formed, while the remainder of the sample passes to the far end, assisting with capillary action.

Many test strip models also include a different chemical at a "control line" position downstream of the one designed to detect the analyte. This second chemical means reacts to all compounds by forming its own stain line, thus indicating to the user that sufficient sample quantity was introduced.

If a stain line is identified by the user, the analyte is considered as present within the liquid sample. However, owing to low concentration and/or other factors, the stain line can be indistinct or almost invisible, causing determination to be difficult and/or unreliable, especially for the non-expert user. Even expert users can have difficulty, and it may be critical for each particular test to register a definitive outcome. Even worse than discarding a test, it may be interpreted incorrectly. Owing to manufacturing tolerances in the test strip, which may require a very low cost, the test stain line may be slightly spread instead of being confined to a distinct location. Therefore, professional laboratories sometimes use high priced image analysis equipment or reflected light instrumentation to capture very light and/or indistinct test stain lines.

The purposes of the inventions described in the instant disclosure are to achieve the superior analysis capabilities of expensive optical analysis equipment using a readout method and apparatus that could eliminate the need for visual inspection, detect analyte concentration far below that of visual inspection and even camera image analysis, and be so inexpensive that they are readily available for all medical offices and nearly all consumers for home use. It is understood that detection of analyte at lower concentrations can permit knowledge of pregnancy, influenza, or other conditions at earlier times, when there are additional advantageous options for treatment and/or prevention of spread. The positive impact on society of such widespread use capability should not be underestimated. Witness the revolution in diabetes care that resulted from accurate home testing of blood glucose levels.

BRIEF SUMMARY

This Brief Summary is provided as a general introduction to the Disclosure provided by the Detailed Description and Figures, summarizing some aspects of the disclosed invention. It is not a detailed overview of the instant disclosure and should not be interpreted as necessarily identifying key elements of the invention, or otherwise characterizing the scope of the invention disclosed in this Patent Document.

Returning to the long-existing Lateral Flow Assay method, a liquid sample, that may or may not contain a target chemical compound, "analyte" is applied close to one end of a test strip consisting of absorbent material that draws the sample by capillary action through its entire length thereof, wetting the strip as it proceeds. There are two major positions along the strip. At the first position is a predeposited first compound that changes its chemical composition only if the analyte compound is present. This first compound is carried with the sample fluid to the second major position whether or not the keyed analyte is present, i.e. whether or not its composition is changed. The second major position, called the test line position is pre-deposited with a second chemical compound that is fixed at this position. If the first compound is in an unchanged composition state, it is not attracted to the second compound and is carried to the far end of the strip by the sample fluid. If the first compound is in a changed composition state, it is attracted to the second compound, and collects at the test line position, causing a reaction of the second compound that creates a colored stain line that is visible upon inspection as a positive test for presence of the analyte.

Instead of requiring visual inspection or camera image analysis, which is useless when the analyte concentration is small enough that accumulation of staining compound is only inside the test strip, the methods taught in the instant disclosure measure the amount of decrease of light passing through the test strip at the test line region, without regard to the location of stain line compound—outside or inside of the test strip. Therefore, a positive test result is achievable even when the targeted condition is present but with analyte concentration having insufficient quantity for the stain line material to reach the test strip surface. Thus, a positive test result can be registered under conditions that are detectable by neither visual nor automated image inspection.

By projecting light toward one side of the strip, measuring how much light emerges on the opposite side, and comparing extinction at the test line region with that at adjacent regions, very small staining compound concentrations are detected. Moreover, by choosing a wavelength that is absorbed by the staining compound and varying the intensity of the incident light, the total amount of this compound is measured, not just the area of a shadow. The result is a wide dynamic range quantitative measurement, with an ability to distinguish small changes whether there is a large amount of staining compound or minute amount. Additionally, by providing color and intensity that varies depending upon illumination of the test line region and adjacent regions, additional sensitivity can be achieved.

Finally, as a means to gather additional information, electronic sensors and instrumentation are capable of dynamic measurements during the wicking process instead of a single measurement when wicking is complete.
Other aspects, features and advantages of the invention will be apparent to those skilled in the art from the following Disclosure.

BRIEF DESCRIPTION OF DRAWINGS

For a more complete understanding of this disclosure and its features, reference is now made to the following description, taken in conjunction with the accompanying drawings, in which.

DETAILED DESCRIPTION

The various figures, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

In general, this disclosure teaches a means to measure the existence and concentration of analyte present in the liquid sample of a lateral flow test strip, by projecting light toward one side of the strip, measuring the quantity of light that emerges on the opposite side, and comparing the extinction caused by the staining compound at the test line region with that at adjacent and other regions.

Depending on the implementation, this technique can provide significant benefits in a range of fields, such as chemical analysis for medical and industrial applications, especially in locations lacking requisite skilled personnel or equipment.

Figure 1:
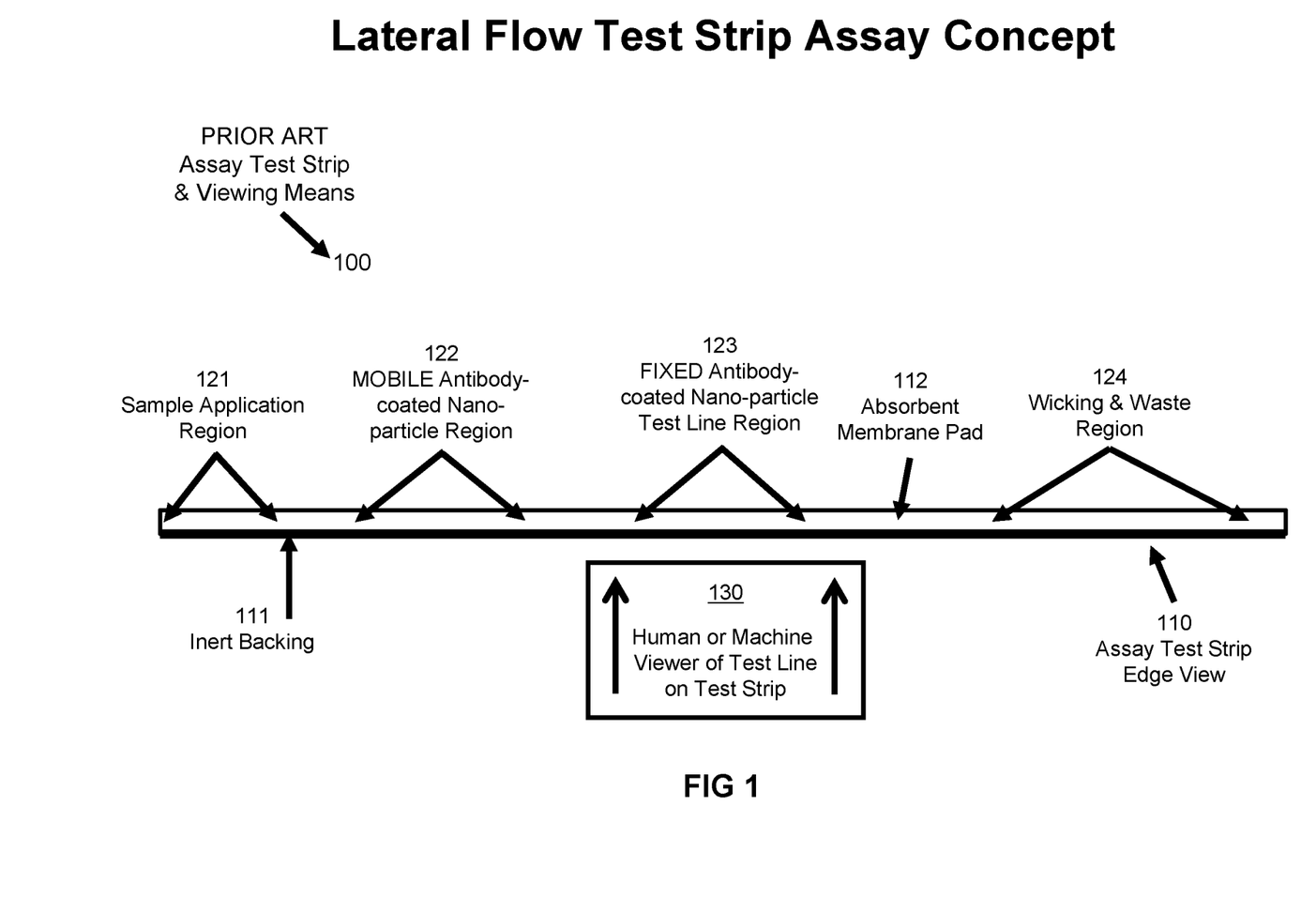
FIG. 1 illustrates an example prior art lateral flow assay test strip system used to determine the presence or absence of a chosen substance.

FIG. 1 illustrates an example prior art Lateral Flow Assay test strip system 100 used to determine the presence or absence of a chosen substance, also known as the analyte, within a liquid. Said test strip consists of a chemically inert backing 111 that may also provide physical strength and stability, and an attached absorbent membrane 112, whose function is to transport liquids from sample application region 121 to wicking and waste region 124, after passing through regions 122 and 123 described below.

Located in region 122 is a deposition of non-reactive metallic or non-metallic nanoparticles that are coated with an antibody substance that is specifically chosen to conjugate with the analyte. These nanoparticles are not permanently attached to the absorbent membrane and will therefore be carried by the fluid sample as it travels along the membrane. Clustered near the center of region 123 is a deposition of identical coated nanoparticles, but in this case, they are permanently attached to the absorbent membrane and will not travel with the sample fluid. The region to the right of region 123, especially region 124, is used to as an extension of the strip to help draw the sample fluid through Region 123 via capillary action and to provide a storage location for the sample fluid and waste products.

If the sample fluid applied at region 121 does not include the analyte, when it reaches region 122, the antibody substance is unchanged as the nanoparticles travel with the sample fluid to region 123. When they arrive at region 123, they do not react with or attach to the nanoparticles there and continue to travel with the sample fluid to region 124.

If the sample fluid applied at region 121 contains the analyte that corresponds with the antibody substance coating the nanoparticles present at regions 122 and 123, there is a different scenario. When the sample fluid reaches region 122, it carries the nanoparticles toward region 123 as in the previous case, but at region 122 and during the travel to region 123, the analyte, according to its concentration, reacts ("conjugates") with the antibody substance on some fraction of the nanoparticles.

When the nanoparticles reach region 123, remaining conjugated but unattached coated nanoparticles attach themselves to the immobile unconjugated coated nanoparticle there. These nanoparticles are therefore trapped in region 123 and accumulate, creating a visible line that indicates presence of the Subject Analyte in the sample fluid. This visible line can be viewed by Human or machine/instrumented viewing means 130.

Test strip 110 is normally contained within an enclosure (not shown), having a suitable opening at sample application region 121 to apply a sample. There is also a transparent region of the enclosure, sometimes referred to as a results window, at test line region 123. Human or machine viewer 130 is shown on the side of test strip 110 that includes backing 111, in which case backing 111 material in region 123 would be transparent. The results window and human or machine viewer 130 could instead be located on the opposite face of test strip 110, whereby inert backing 111 would not need to have a transparent region.

Figure 2:
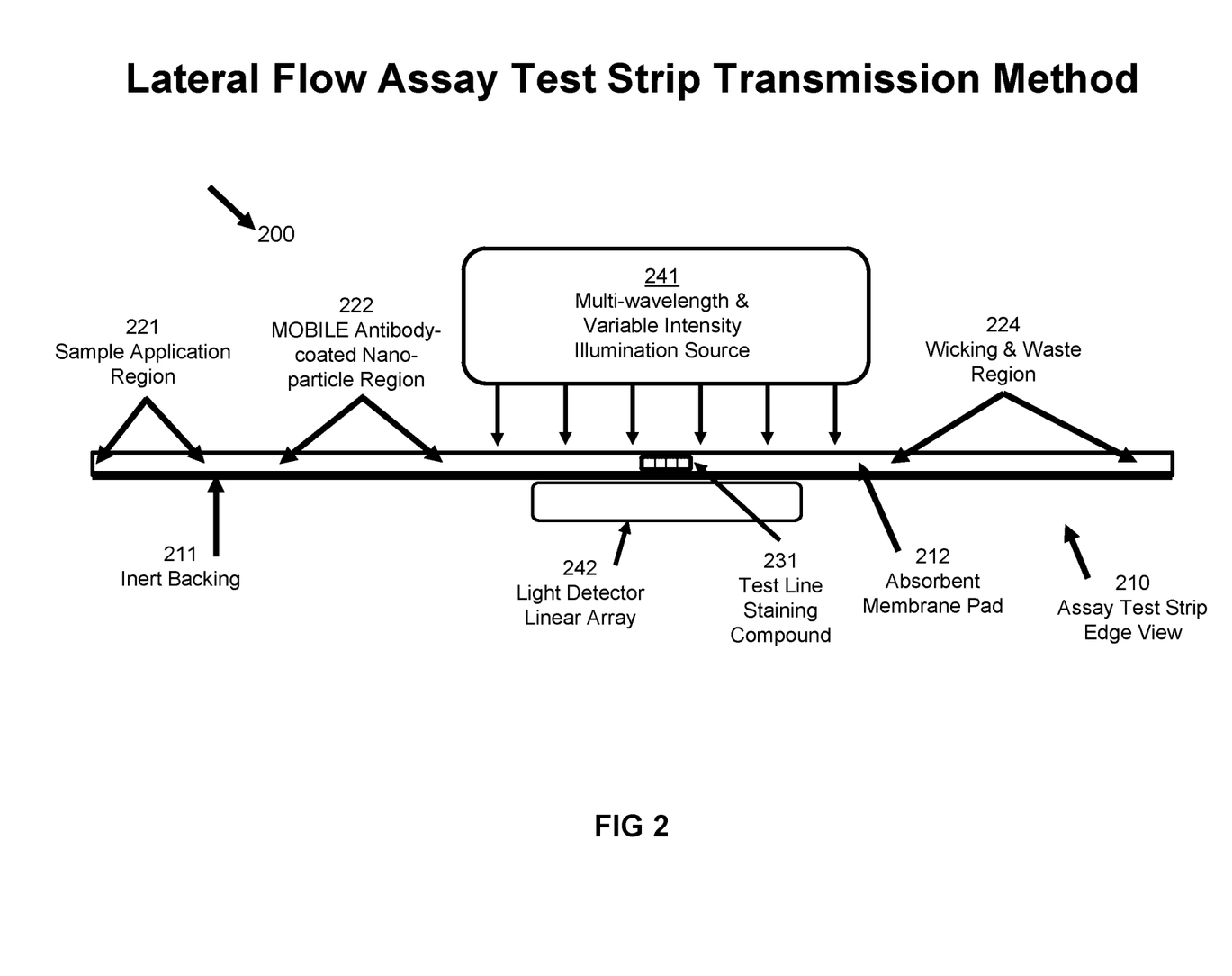
FIG. 2 shows the example lateral flow assay test strip of FIG. 1 but replaces the human, incident light reflected, or camera-based image analyzer with an illumination source on one side of test strip and light detector on the opposite side.

FIG. 2, a novel approach, illustrates an example method to employ the same lateral flow assay test method but register the result without need for manual or instrumented optical inspection. Moreover, quantitative measurements of the analyte are further facilitated.

FIG. 2 replaces the human, incident light reflected, or camera-based image analyzer with an automated reader instrument consisting mainly of an illumination source 241 projecting on either face of test strip 210 and light detector array 242 at its opposite face. Illumination source 241 and light detector 242 could be separate equipment units or contained within an integrated test fixture (not shown). Inert backing 211 could be transparent, especially in the region containing light detector array 242. Illumination source 241 illuminates enough of test strip 210 to cover the region where the staining compound 231 can accumulate, plus the adjacent regions for comparison. Illumination source 241 could provide light having a multiplicity of wavelengths and a multiplicity of intensities. Wavelength and intensity could vary with time, position along the test strip, or both.

Light detector 242 could consist of a linear array of many individually addressable optical detector "pixels". These detector pixels are normally broadband but could also have narrow band spectral response. The detectors in array 242 are very close to the test strip surface, permitting intensities to be measured without need for optical focusing components. By reading separate light values at each position along the test strip, an extinction curve can be generated to be used to derive analyte sample presence and concentration.

By projecting light toward one side of test strip 210, measuring how much light emerges on the opposite side, and comparing extinction at the test line region with that at other regions, very small staining compound concentrations are detected. Moreover, by choosing a wavelength that is absorbed by the staining compound and varying the intensity of the incident light, the total amount of this compound is measured, not just the area of a shadow. Additionally, by providing wavelength and intensity that varies depending upon illumination of the test line region and adjacent regions, additional sensitivity can be achieved.

Moreover, through use of variable intensity and wavelength lighting, this method is applicable to a wide variety of test strip analyte chemical processing and test stain line development processes, all using a single instrument model.

While the preceding paragraphs and FIG. 2 describe a multi-wavelength illumination source coupled through a lateral flow test strip to a broadband light detector, it may be advantageous under some circumstances to employ a broadband illumination source and selective wavelength detectors, also known as spectrometers. In such case, block 241 would be labeled "Broadband Variable Intensity Illumination Source", and block 242 would be labeled "Spectrometer Array".

Figure 3:
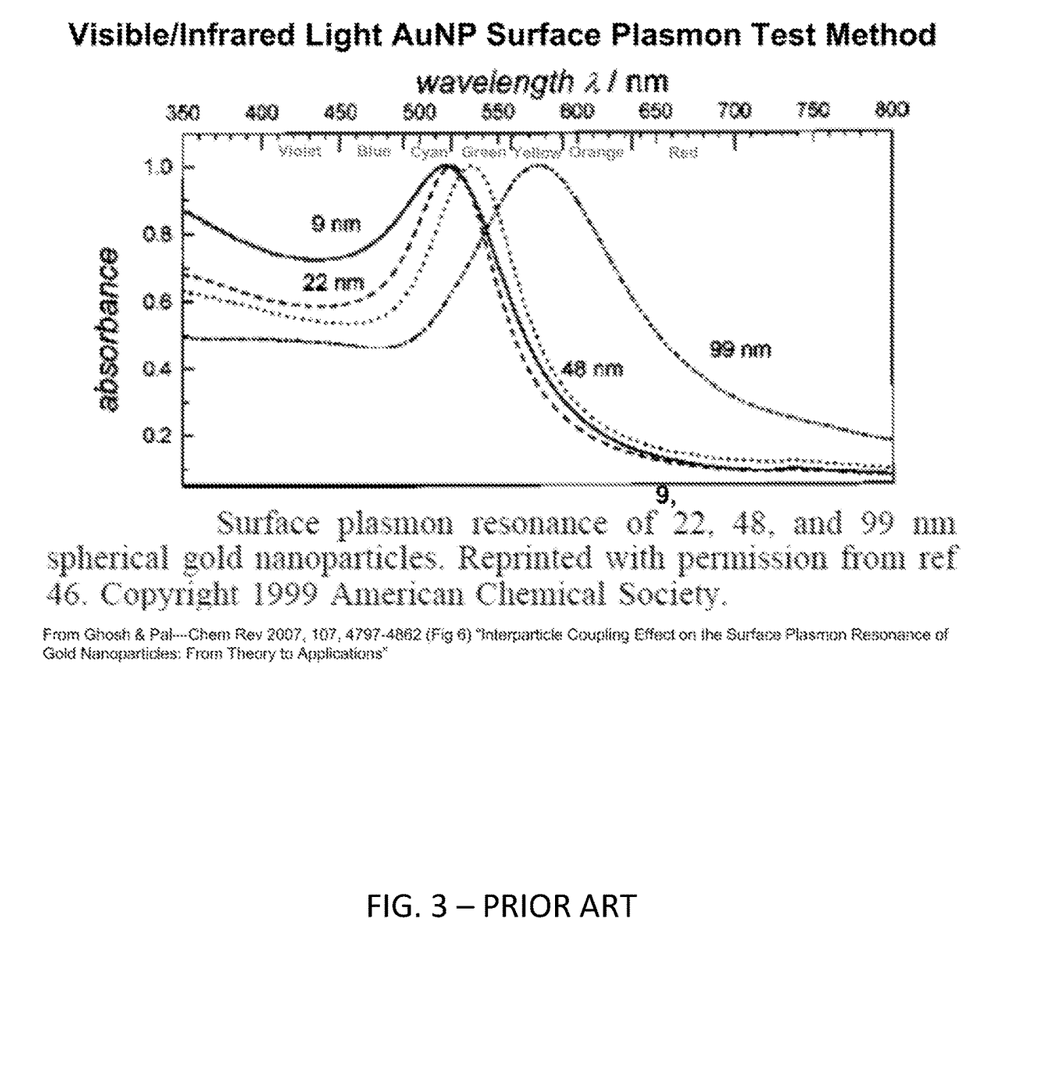
FIG. 3 shows absorbance as a function of wavelength obtained by variations of an example critical material type used in some lateral flow test strip products.

FIG. 3 shows absorbance as a function of wavelength obtained by variations of an example critical material type used in some lateral flow test strip products. It demonstrates the idea that by choosing the optimal illumination source color, lower analyte concentrations are measurable.

Figure 4:
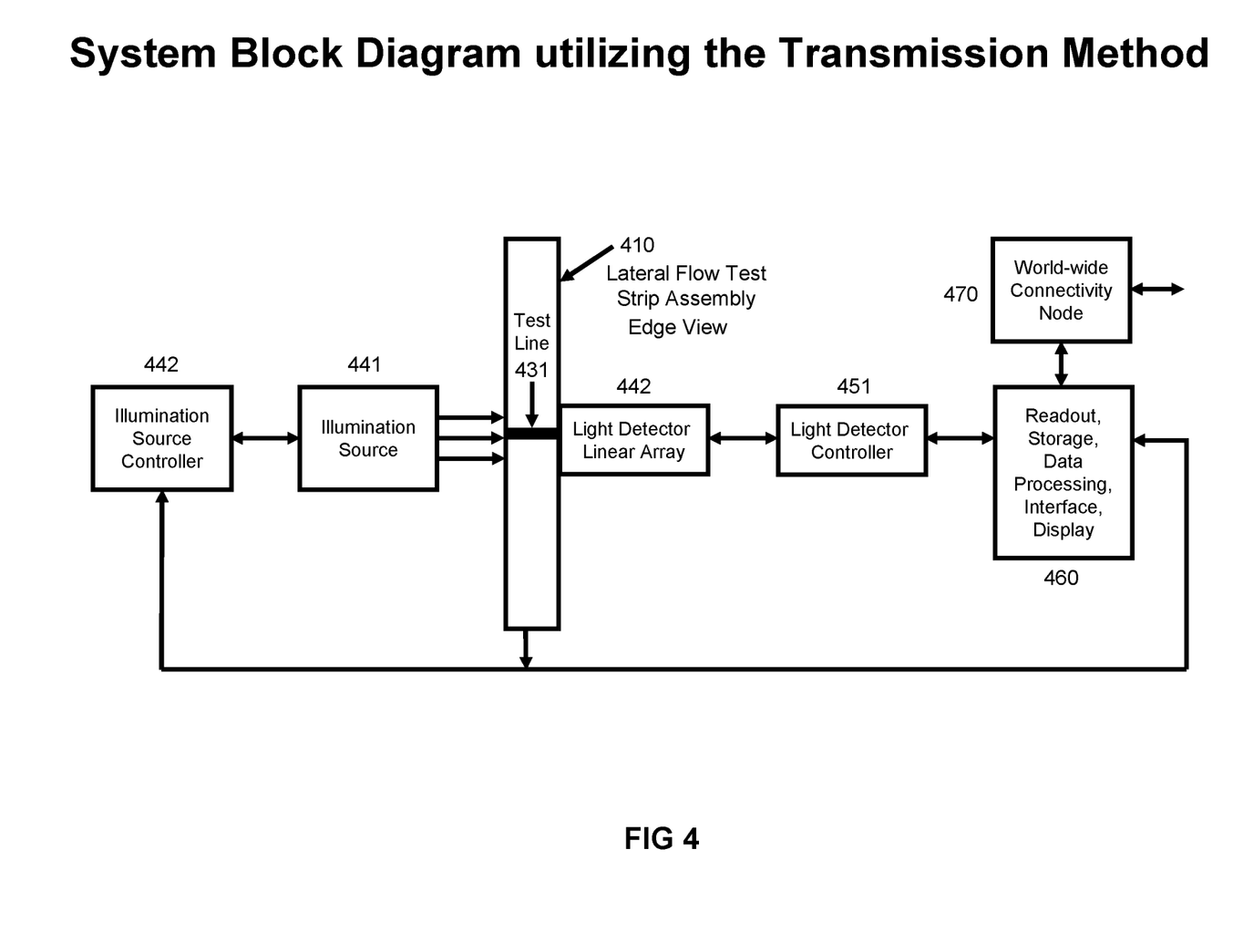
FIG. 4 shows a system block diagram of the lateral flow assay test strip method depicted in FIG. 2.

FIG. 4 shows a system block diagram of the reader instrument method. The illumination source controller 442 controls the wavelength and intensity of illumination source 441 in order to provide the most suitable wavelength and intensity as a function of position directed toward one face of test strip assembly 410. Test stain line 431, depending upon the amount of analyte concentration, partially obscures light reaching the opposite face of test strip assembly 410. Light detector linear array 442, operated by light detector controller 451, registers the amount of transmitted light as a function of position covering the test stain line and the regions adjacent to it.

Illumination source 441 could have controlled and variable intensity and wavelength as stated above, or the source could be broadband. Light detector 442 could have a broadband response as stated above or consist of wavelength-selective spectrometer elements.

Main processing unit 460 coordinates operation of the controllers, receives serial number data from test strip assembly 410, calculates analyte concentration levels, and communicates with and controls world-wide connectivity node 470.

World-wide connectivity node 470 receives analyte concentration data, date, time and test strip assembly serial number from main processing unit 460, as well as location data from GPS or other location services. It transmits in real time this information for traceability and to assist networks to track data in general and especially the spread of diseases.

Figure 5:
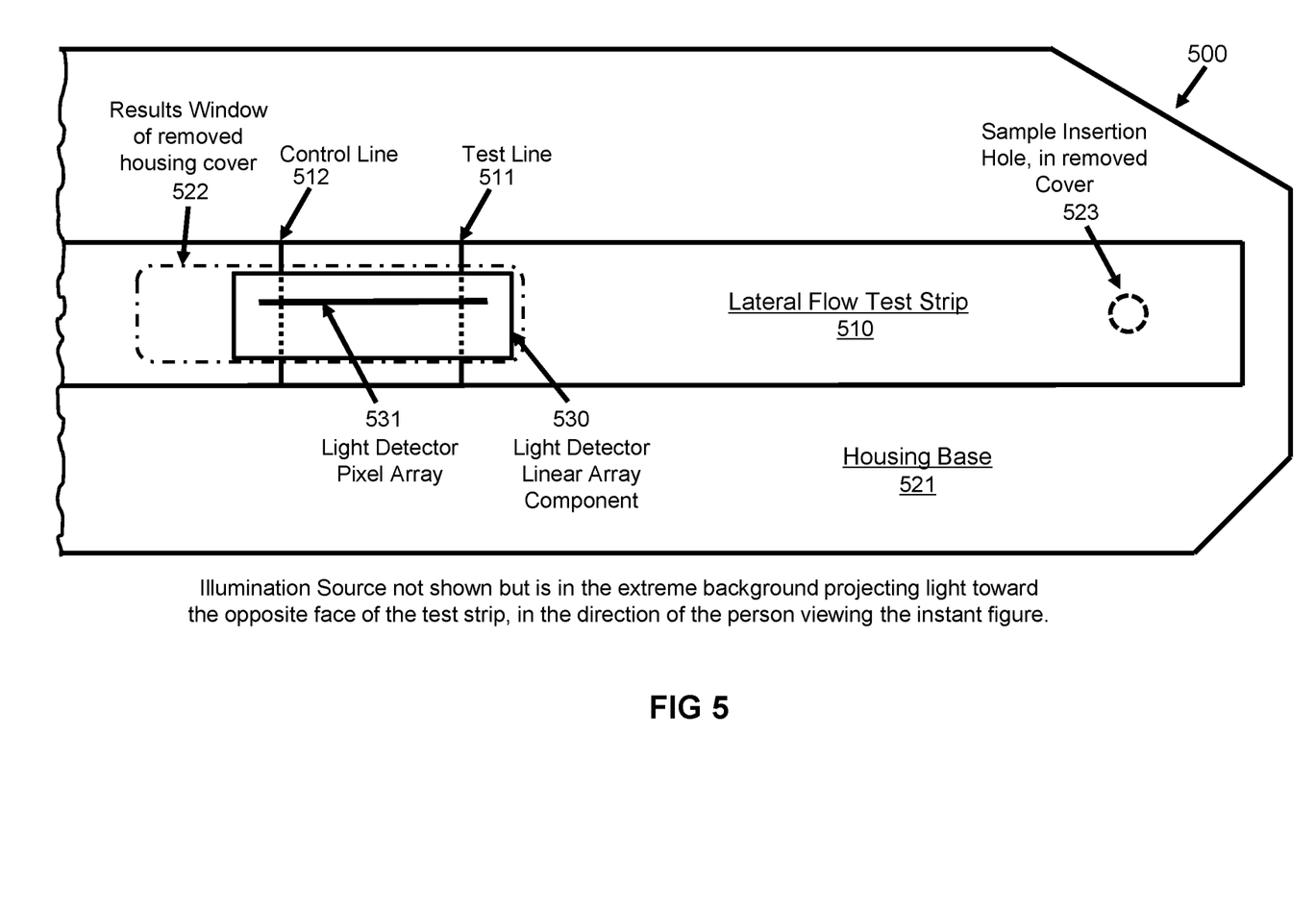
FIG. 5 shows a section of a lateral flow test strip housing with its cover removed, also showing a section of its test strip and components of an automated instrument to determine the presence of analyte indicators.

FIG. 5, 500 shows a section of a lateral flow assay test strip assembly attached to components of an automated reader instrument as described in FIG. 4. The lateral flow assay test strip assembly could consist of a lateral flow test strip 510, a housing base 521 and a housing cover (not shown) removed. At the right-hand end of test strip 510 is a dotted circle 523 representing the hole in the removed housing cover, through which the liquid sample is injected to wet test strip 510. In this view of the example construction, test strip 510 is in the background with the transparent inert backing 210 facing the person viewing this figure. Therefore, there is no inert backing 210 material in the region of the sample insertion hole 523.

In the region of results window 522 located on housing cover, not shown, test strip 510 and its stain lines, 511 and 512, are visible through its transparent inert backing 210, except where hidden by light detector linear array component 530, part of the automated reader instrument, in the extreme foreground. The light detector pixel array 531, part of the linear array component 530, is on the bottom surface of this component, resting on inert backing 210. If the housing cover were in place, the linear array component would still be positioned as shown, within results window 522.

The illumination source, not shown, another part of the automated reader instrument, is in the extreme background projecting light toward the opposite face of test strip 510, in the direction of the person viewing this figure. The light from this source may reach the test strip through a transparent slot, not shown, in housing base 521. If there is no slot, light still reaches test strip 510 if the housing base material is translucent.

Illumination characteristics need to be very flexible in order to detect the smallest analyte concentrations. It is important to make on-the-fly adjustments for optimum light color and intensity distribution throughout the test strip test line and adjacent regions. It cannot even be assumed that the test strip opacity, irrespective of the stain line, is uniform throughout the relevant dimensional range or even within the critical region of this range.

Such advanced illumination controller methodology allows adjustment to as high a resolution function of position as permitted by the detector array, the light wavelength and 500,000 steps of illumination intensity. This is achieved with the aid of a linear and pulse-width modulated dimming approach implemented in a closed loop. Leveraging this illumination controller methodology allows one to compensate for nonlinear effects as described in the next paragraph, leading to increased accuracy.

Excitation current step resolution quantifies light extinction. The technique involves choosing an advantageous fiduciary value of post-transmission light intensity, adjusting the illumination level so that the null created by the test stain line is at the fiduciary level, and using the illumination level as the post transmission light intensity scale, where this scale can be mapped to an analyte concentration scale. This technique is completely agnostic to the composition and dimension of nanoparticles present within the test strip and eliminates the need for a high-resolution signal voltage scale.

Figure 6:
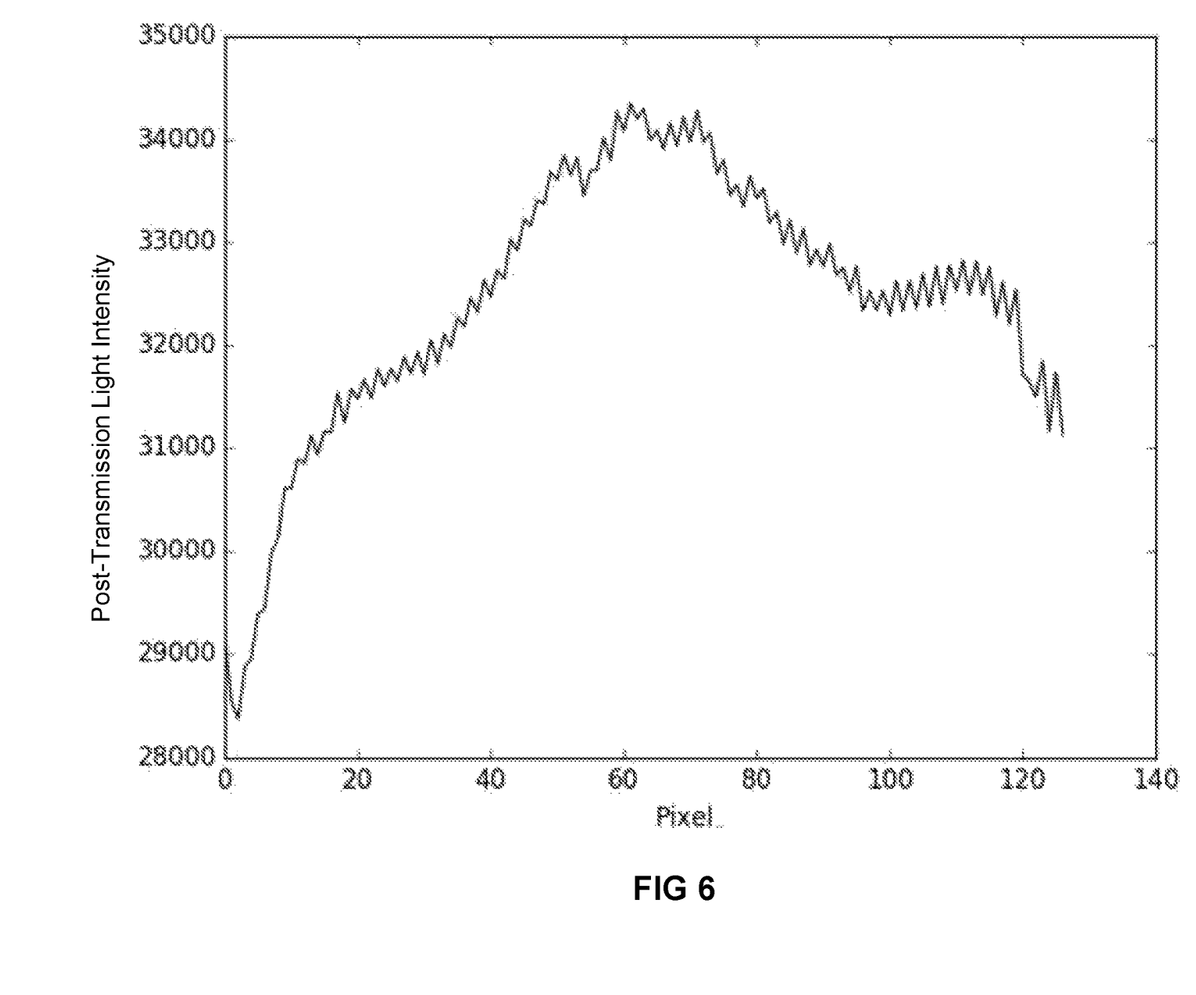
FIG. 6 shows an extinction scan of an unused, dry lateral flow assay test strip.

FIG. 6 shows an extinction scan made with an unused, dry lateral flow assay test strip. The numbers of the horizontal scale represent the pixel number of light detector pixel array 531 and therefore the relative location along lateral flow assay test strip 510. Overall, there is little extinction and extinction variation, as indicated with the help of the narrow range of the light intensity scale. The extinction pattern could be an indication of the opacity of materials distributed within the strip.

Figure 7:
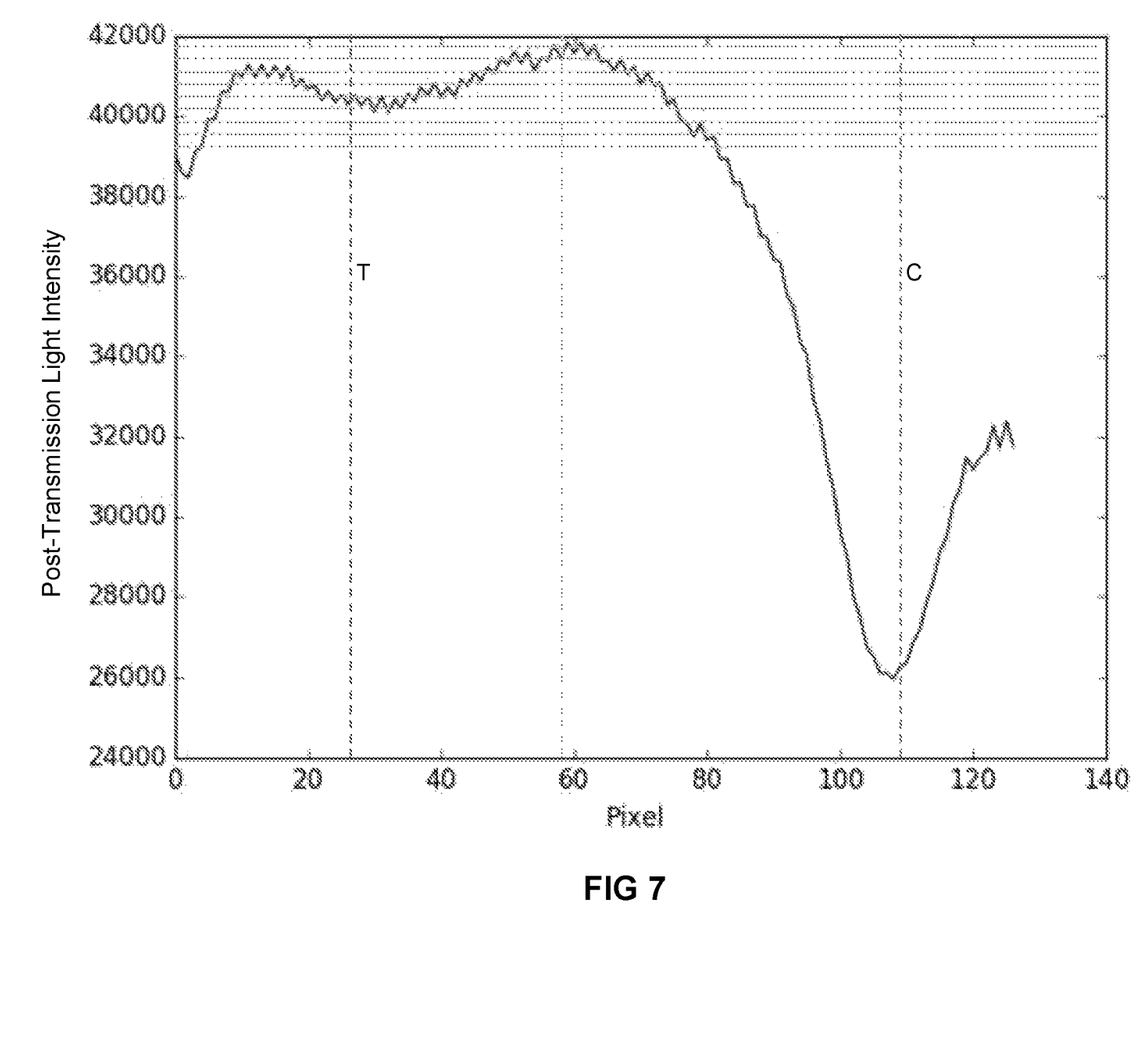
FIG. 7 shows a measurement result from a "negative" test (zero analyte) but showing the positive control line.

FIG. 7 shows a measurement result from a "negative" test (zero analyte). The major feature centered on pixel ∩108 ("C") is from the control line, indicating that a valid test was executed. The very minor feature centered on Pixel ∩30 is due either to illumination that is not quite uniform or minor additional opacity of the test strip owing to non-activated nanoparticles that have been washed slightly downstream from the nominal test stain line region (shown as "T"). Regardless, the illumination control means described above can be used to cause this region of the scan to be flat, facilitating detection of analyte concentrations below the level shown in in FIG. 8.

Figure 8:
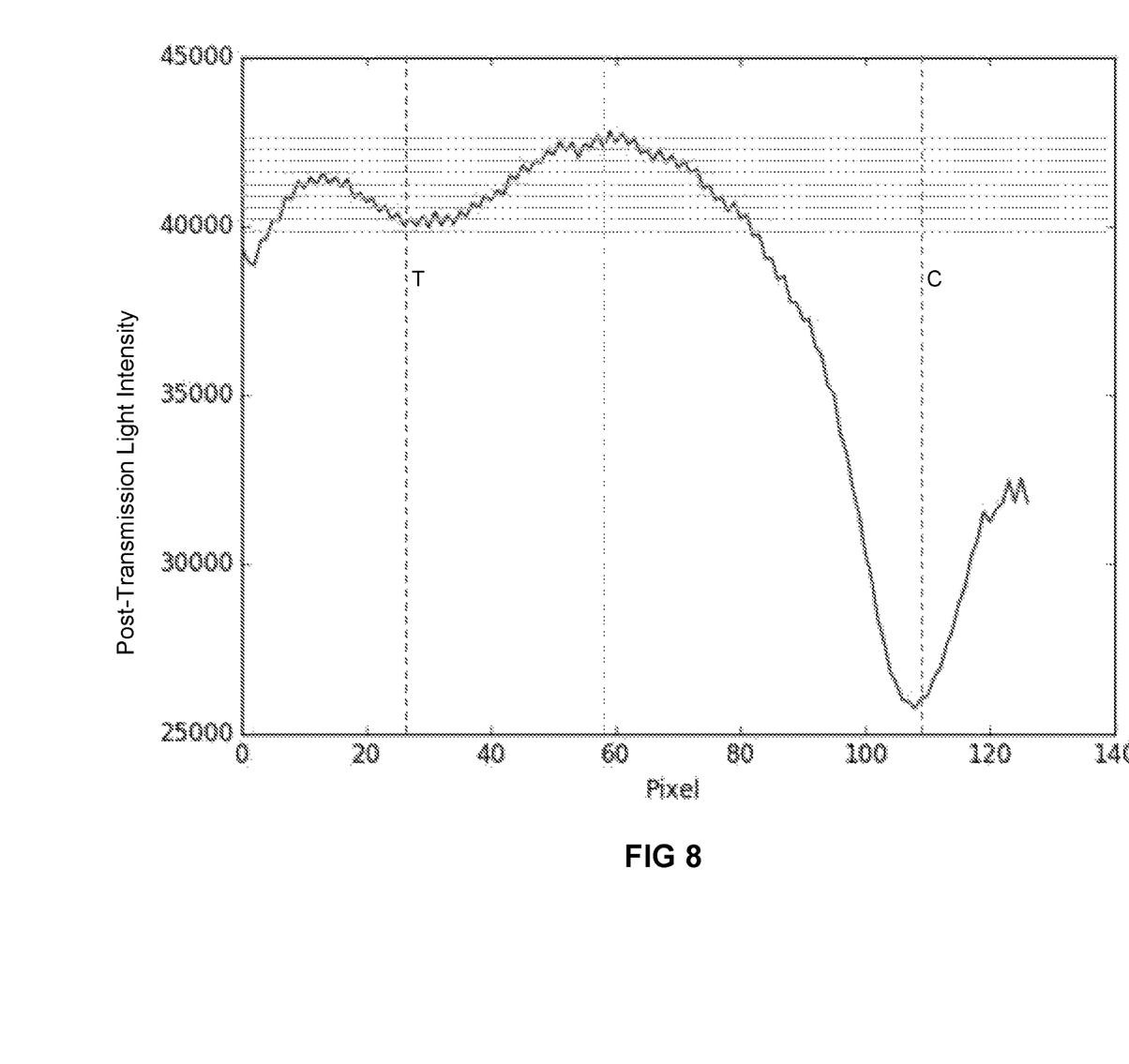
FIG. 8 shows the measured result of a sample analyte concentration that is close to the instrument Limit of Detection (LOD) but whose test stain line is absent from the test strip surface.

FIG. 8 shows a measurement of a sample analyte concentration that is close to the Limit of Detection (LOD). For this concentration, there is no visible test stain line whatsoever when observing the test strip with the naked eye or with artificial intelligence-equipped video equipment.

In order to detect concentrations at the limit of detection, mathematical analysis leveraging ratio-metric techniques in conjunction with artificial intelligence incorporated in this instrument can be used, as opposed to only measuring amplitudes. The analysis can take into account all portions of the curve between, say, pixels 8 and 75.

Figure 9:
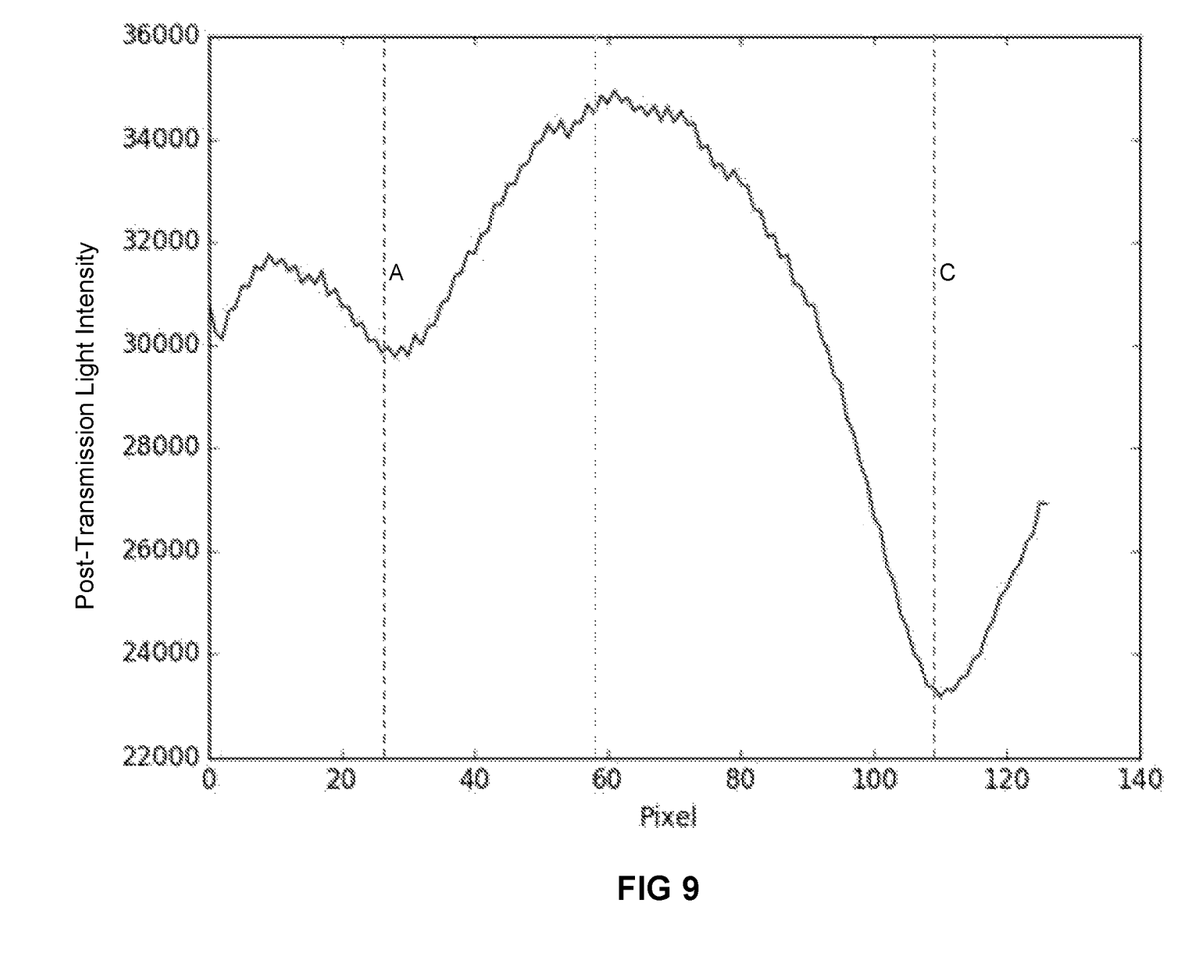
FIG. 9 shows the measured result for analyte concentration double that shown in FIG. 10 and whose test stain line almost totally invisible on the test strip surface.

At the analyte concentration double that shown in FIG. 8, resulting in the curve shown in FIG. 9, the stain line appears to be just barely visible when the test strip itself is very carefully observed with the naked eye, as some indication of the threshold level for the reflected light, and camera/image analysis method now in prevalent use.

Figure 10:
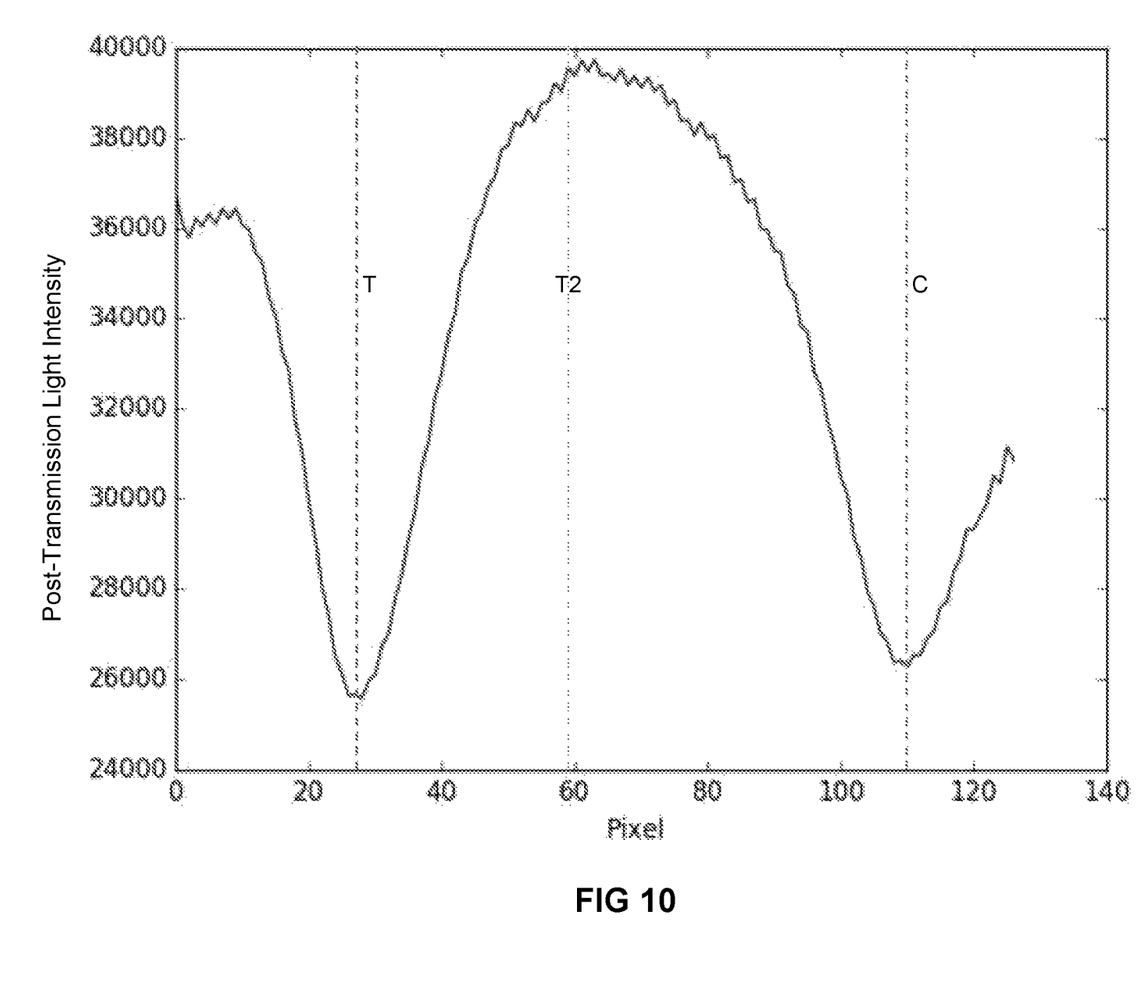
FIG. 10 shows the measured result for analyte concentration eight times that shown in FIG. 10.

FIG. 10 shows the measured result for an analyte concentration eight times that shown in FIG. 8. There is no sign of compression. Also, there is sufficient test line position resolution to accommodate a second analyte whose stain line, T2, would appear at Pixel ∩60.

The details provided in the above description describe particular implementations of the systems for performing the measurements described. Other embodiments could be implemented in any other suitable manner. For example, particular voltages, frequencies, noise levels, gains, resistances, capacitances, and other values may be described. These values are for illustration only. It may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method to automatically detect an analyte in a liquid sample in a lateral flow assay test strip by evaluating a stain line of said test strip, said test strip comprising an upper testing surface and a lower inert backing surface opposing said upper testing surface, the method comprising:
    illuminating said upper testing surface of said test strip using a light source that faces said upper testing surface;
    situating a light detector consisting of a linear array of individually addressable optical detector pixels lengthwise along a portion of said lower inert backing surface of said test strip such that said light detector rests on said portion of said lower inert backing surface;
    evaluating said stain line to automatically detect a presence of said analyte by processing light values from said detector pixels from said light detector irrespective of whether said stain line is visible to a naked eye when viewing said upper testing surface;
    wherein, no focusing component is provided between said light source and said light detector.

2. The method of claim 1, further comprising programmatically varying a wavelength and an intensity of the light source.

3. The method of claim 2, further comprising programmatically varying the wavelength and the intensity of the light source as a function of longitudinal position along said test strip.

4. The method of claim 1, further comprising injecting said liquid sample to said test strip.

* * * * *